United States Patent [19]

Ling et al.

[11] Patent Number: 5,041,538

[45] Date of Patent: Aug. 20, 1991

[54] MAMMALIAN FOLLISTATIN

[75] Inventors: Nicholas C. K. Ling, San Diego, Calif.; Naoto Ueno, Ibaraki, Japan; Shunichi Shimasaki, San Diego; Frederick S. Esch, Forest City; Shao-Yao Ying, San Diego; Roger C. L. Guillemin, La Jolla, all of Calif.

[73] Assignee: The Salk Institute for Biological Studies, San Diego, Calif.

[21] Appl. No.: 224,432

[22] Filed: Jul. 26, 1988

Related U.S. Application Data

[63] Continuation-in-part of Ser. No. 90,635, Aug. 28, 1987, abandoned.

[51] Int. Cl.$^5$ .............................................. C07K 13/00
[52] U.S. Cl. .................................. 530/395; 530/397; 530/387; 530/350
[58] Field of Search ................ 530/395, 350, 357, 397

[56] References Cited

U.S. PATENT DOCUMENTS 4,624,944 11/1986 Li et al. ................................. 514/12

OTHER PUBLICATIONS

Shimasaki et al., Porcine Follistatin Gene Structure Supports Two Forms of Mature Follistatin, Biochem & Biophys. Res. Comm 152(2) 717-723 (1988).

diZerega et al., "Identification of Protein(s) Secreted by the Preovulatory Ovary which Suppresses the Follicle Response to Gonadotropins," *J. Clin. Endocrinol. and Metab.,* 54: 1091-1096 (1982).

Kling et al., "Identification of Procine Follicular Fluid Fraction which Suppresses Follicular Response to Gonadotropins," *Biology of Reproduction,* 30: 564-572 (1984).

Mason et al., "Complementary DNA Sequences of Ovarian Follicular Fluid Inhibin Show Precursor Structure and Homology with Transforming Growth Factor-$\beta$," *Nature,* 318: 659-663 (1985).

Mason et al., "Structure of Two Human Ovarian Inhibins,"0 *Biochem. & Biophys. Res. Commun.,* 135: No. 3, 957-964 (1986).

Forage et al., "Cloning and Sequence Analysis of cDNA Species Coding for the Two Subunits of Inhibin from Bovine Follicular Fluid," *Proc. Natl. Acad. Sci. U.S.A.,* 83: 3091-3095 (1986).

*Primary Examiner*—Margaret Moskowitz
*Assistant Examiner*—Shelly J. Guest
*Attorney, Agent, or Firm*—Fitch, Even, Tabin & Flannery

[57] ABSTRACT

Two follistatin proteins with inhibin-like activity were isolated from porcine follicular fluid using heparin-Sepharose affinity chromatography, followed by gel filtration on Sephacryl S-200 and then six steps of high-performance liquid chromatography. Each isolated molecule is a monomer having a molecular weight of at least about 32,000 daltons. Microsequencing revealed the $NH_2$-terminal portions both to be Gly-Asn-Cys-Trp-Leu-Arg-Gln-Ala-Lys-Asn-Gly-Arg-Cys-Gln-Val-Leu. The larger protein has 315 residues and is believed to be glycosylated. The smaller protein is a 288-residue, C-terminally shortened version thereof. These proteins specifically inhibit basal secretion of FSH, but not of LH, in a rat anterior pituitary monolayer culture system. The Half-maximal effective dose for both is 2.5-6.0 ng/ml. Human and rat follistatins exhibit very high homology with the porcine protein, with the human differing from porcine in only 4 residues out of 315 and with the rat differing from porcine in only 8 residues out of 315.

16 Claims, 5 Drawing Sheets

```
                                                                      +300
1261 GAGGAAGAGGAGGAAGATGAAGACCAGGACTACAGCTTCCTATATCTTCTATTCTAGAGTGGTAAACTCTCTATAAGTGTTCAGTGTTC 1350
      E   E   E   D   E   D   Q   D   Y   S   F   P   I   S
                                                                                +310
1351 ACATAGCCTTTGTGCAAAAACTATACATTAAGGACCCTTTGTCCTAAGCTCTCTCCCAGGCAGAAAATATATTGTCCATAGTGTATGCTTA 1440
      I   L   E   W end
1441 TTTATTGTGAGGTGAGGTCTACTGACTGAGAGCCCATGATGAGACTTGAGACTTGTAGACATTATTATACTGTACTTGTAAATAAGTGTATGCTTA 1530
                                                                       ... ACCTTGTTACTCATTGTTACTCTGTTTATAATTATACATAAA
1531 TTCATTGTGAGGTCTACTGACTGAGAGCCCATGATGAGACTTGAGACTTGTAGACATTATTATACTGTTTATAATTATACATAAA 1620
1621 TGTCTGGTGACTGTACTTGTATACCTTGTTTGAAGAAATTATTCGGAAGAAGACAGTGTTATTATGGAGGTCTCTTGCTTGTAA 1710
1711 AGTAAAGCTTTTTCCTTGTAAACCATTAAGTCCATTCACTCACTCATCTGTCCCTTCATTCACTGTTAGACTC 1800
1801 TTTTCCACTTGTTTCAACAAACTGCATGTCAGTTCTGTCATGTTATTTTATTGGATTCTGCTGTACATACATGATCCCTC 1890
1891 GGGTTTGTTACAAGGAACCTTGACTGACTGACCAAAGGCATTATAACTCTGACTCAAATACAAGGTACAGAAGATAAGCATCTTTGAGGAA 1980
1981 ACTCCTACTTCAGTTCTTTTGTTATGATGAAGACATTTGT                                            2020
```

FIG. 4

```
                                                              ATG GTC CGC
                                                              MET Val Arg
                                                    54
GCG AGG CAC CAG CCG GGT GGG CTT TGC CTC CTG CTG CTG CTG CTC TGC CAG TTC
Ala Arg His Gln Pro Gly Gly Leu Cys Leu Leu Leu Leu Leu Leu Cys Gln Phe
Pro Lys
                                                    108
ATG GAG GAC CGC AGT GCC CAG GCT GGG AAC TGC TGG CTC CGT CAA GCG AAG AAC
MET Glu Asp Arg Ser Ala Gln Ala Gly Asn Cys Trp Leu Arg Gln Ala Lys Asn
                    -1  +1
                                                    162
GGC CGC TGC CAG GTC CTG TAC AAG ACC GAA CTG AGC AAG GAG GAG TGC TGC AGC
Gly Arg Cys Gln Val Leu Tyr Lys Thr Glu Leu Ser Lys Glu Glu Cys Cys Ser
                                20
                                                    216
ACC GGC CGG CTG AGC ACC TCG TGG ACC GAG GAG GAC GTG AAT GAC AAC ACA CTC
Thr Gly Arg Leu Ser Thr Ser Trp Thr Glu Glu Asp Val Asn Asp Asn Thr Leu
                                    40
                                                    270
TTC AAG TGG ATG ATT TTC AAC GGG GGC GCC CCC AAC TGC ATC CCC TGT AAA GAA
Phe Lys Trp MET Ile Phe Asn Gly Gly Ala Pro Asn Cys Ile Pro Cys Lys Glu
            50
                                                    324
ACG TGT GAG AAC GTG GAC TGT GGA CCT GGG AAA AAA TGC CGA ATG AAC AAG AAG
Thr Cys Glu Asn Val Asp Cys Gly Pro Gly Lys Lys Cys Arg MET Asn Lys Lys
                        70
                                                    378
AAC AAA CCC CGC TGC GTC TGC GCC CCG GAT TGT TCC AAC ATC ACC TGG AAG GGT
Asn Lys Pro Arg Cys Val Cys Ala Pro Asp Cys Ser Asn Ile Thr Trp Lys Gly
                                90
                                                    432
CCA GTC TGC GGG CTG GAT GGG AAA ACC TAC CGC AAT GAA TGT GCA CTC CTA AAG
Pro Val Cys Gly Leu Asp Gly Lys Thr Tyr Arg Asn Glu Cys Ala Leu Leu Lys
                                    110
                                                    486
GCA AGA TGT AAA GAG CAG CCA GAA CTG GAA GTC CAG TAC CAA GGC AGA TGT AAA
Ala Arg Cys Lys Glu Gln Pro Glu Leu Glu Val Gln Tyr Gln Gly Arg Cys Lys
                                        130                 Lys
                                                    540
AAG ACT TGT CGG GAT GTT TTC TGT CCA GGC AGC TCC ACA TGT GTG GTG GAC CAG
Lys Thr Cys Arg Asp Val Phe Cys Pro Gly Ser Ser Thr Cys Val Val Asp Gln
                    140
                                                    594
ACC AAT AAT GCC TAC TGT GTG ACC TGT AAT CGG ATT TGC CCA GAG CCT GCT TCC
Thr Asn Asn Ala Tyr Cys Val Thr Cys Asn Arg Ile Cys Pro Glu Pro Ala Ser
                            160                             Thr
                                                    648
TCT GAG CAA TAT CTC TGT GGG AAT GAT GGA GTC ACC TAC TCC AGT GCC TGC CAC
Ser Glu Gln Tyr Leu Cys Gly Asn Asp Gly Val Thr Tyr Ser Ser Ala Cys His
                                180
                                                    702
CTG AGA AAG GCT ACC TGC CTG CTG GGC AGA TCT ATT GGA TTA GCC TAT GAG GGA
Leu Arg Lys Ala Thr Cys Leu Leu Gly Arg Ser Ile Gly Leu Ala Tyr Glu Gly
                                    200
                                                    756
AAG TGT ATC AAA GCA AAG TCC TGT GAA GAT ATC CAG TGC ACT GGT GGG AAA AAA
Lys Cys Ile Lys Ala Lys Ser Cys Glu Asp Ile Gln Cys Thr Gly Gly Lys Lys
                                        220
                                                    810
TGT TTA TGG GAT TTC AAG GTT GGG AGA GGC CGG TGT TCC CTC TGT GAT GAG CTG
Cys Leu Trp Asp Phe Lys Val Gly Arg Gly Arg Cys Ser Leu Cys Asp Glu Leu
            230
                                                    864
TGC CCT GAC AGT AAG TCG GAT GAG CCT GTC TGT GCC AGT GAC AAT GCC ACT TAT
Cys Pro Asp Ser Lys Ser Asp Glu Pro Val Cys Ala Ser Asp Asn Ala Thr Tyr
        Glu         Glu
                    250
                                                    918
GCC AGC GAG TGT GCC ATG AAG GAA GCT GCC TGC TCC TCA GGT GTG CTA CTG GAA
Ala Ser Glu Cys Ala MET Lys Glu Ala Ala Cys Ser Ser Gly Val Leu Leu Glu
                            270
                                                    972
GTA AAG CAC TCC GGA TCT TGC AAC TCC ATT TCG GAA GAC ACC GAG GAA GAG GAG
Val Lys His Ser Gly Ser Cys Asn Ser Ile Ser Glu Asp Thr Glu Glu Glu Glu
                                290
                                                    1026
GAA GAT GAA GAC CAG GAC TAC AGC TTT CCT ATA TCT TCT ATT CTA GAG TGG
Glu Asp Glu Asp Gln Asp Tyr Ser Phe Pro Ile Ser Ser Ile Leu Glu Trp
                                310
```

MAMMALIAN FOLLISTATIN

This application is a continuation-in-part of our earlier application Ser. No. 90,635, filed Aug. 28, 1987, now abandoned.

The present invention relates to a protein having inhibin-like activity isolated substantially to homogeneity from bodily material obtained from porcine animals and which is referred to as follistatin.

BACKGROUND OF THE INVENTION

The concept of inhibin as a water-soluble substance produced in the gonad but acting specifically at the pituitary level to inhibit the secretion of follicle-stimulating hormone (FSH) was postulated by McCullagh in 1932 (Science. 76, 19-20). Such preferential regulation of the gonadotropin secretion has generated a great deal of interest and has prompted many laboratories in the past fifty years to attempt to isolate and characterize this substance from extracts of testis, spermatozoa, rete testis fluid, seminal plasma and ovarian follicular fluid, using various bioassays. Although many reports have appeared in the literature claiming the purification of inhibin-like material with molecular weights ranging from 5,000 to 100,000 daltons, subsequent studies have shown that these substances were either not homogenous or did not have the high specific activity expected of true inhibin, de Jong, *Molecular & Cellular Endocrin.*, 13, 1-10 (1979). In 1985, the full sequence of two 32K forms of inhibin from porcine follicular fluid (PFF) were discovered and published, Mason, A. J. et al. Nature, 318, 659-663 (1985). Both were dimers of an 18K α-subunit crosslinked with a 14K β-subunit. Materials having inhibin-like activity may be used to regulate fertility in mammalian animals, particularly male animals.

SUMMARY OF THE INVENTION

In accordance with the present invention, two proteins, one having a molecular weight of about 35,000 daltons (35K) and the other about 32,000 daltons (32K) and both having inhibin activity have been successfully isolated from porcine follicular fluid. These two proteins have been completely characterized using microsequencing and molecular biological methods. Using the porcine amino acid sequence information, cDNA clones encoding these proteins were identified from a porcine ovarian cDNA library. Then, using the porcine cDNA as a probe, the cloning and sequencing of the corresponding human and rat proteins were accomplished.

More specifically, the proteins were first isolated and purified to substantial homogeneity from material obtained from the bodies of porcine animals and are hereinafter referred to as Follistatin A and Follistatin B. Each protein is composed of a single polypeptide chain. Microsequencing showed that the amino-terminal amino acid residue sequence of both proteins was Gly-Asn-Cys-Trp-Leu-Arg-Gln-Ala-Lys-Asn-Gly-Arg-Cys-Gln-Val-Leu. It was also ascertained that the next eight residues of Follistatin A were Tyr-Lys-Thr-Glu-Leu-Ser-Lys-Glu. Follistatin A has now been completely characterized as a result of further microsequencing and the use of molecular biological techniques. Each protein exhibits inhibin-like activity in that it specifically inhibits basal secretion of FSH but does not inhibit basal secretion of luteinizing hormone (LH).

Purification of porcine follistatin to substantial homogeneity, i.e., about 90% by weight of total protein in the fraction, was achieved through a combination of protein separation procedures including heparin-Sepharose affinity chromatography, gel filtration and reverse-phase, high-performance liquid chromatography (RP-HPLC).

BRIEF DESCRIPTION OF THE DRAWINGS

FIG. 1 is a group of three chromatograms representing certain initial steps of purifications of follistatin (FS) and other proteins from porcine follicular fluid (PFF) under conditions described as follows:

FIG. 2 shows chromatograms of RP-HPLC purification of follistatin as follows:

FIG. 3 shows nucleotide and deduced protein sequences of human follistatin cDNAs encoding the 317 and 344 amino acid precursors and also shows the five introns from the human follistatin gene; the nucleotides are numbered at the left and the right, and amino acids, in one-letter code, are numbered throughout. The six differences in the porcine protein are shown in parentheses below the line.

FIG. 4 shows only the nucleotide and predicted amino acid sequences of the human follistatin cDNA inserts, with nucleotides numbered at the ends of the lines while amino acids, in three-letter code, are numbered throughout the lines. The six differences in the amino acid sequences between human and porcine follistatin are indicated in the boxes extending below the respective lines.

DETAILED DESCRIPTION OF THE PREFERRED EMBODIMENTS

Figure 1A:
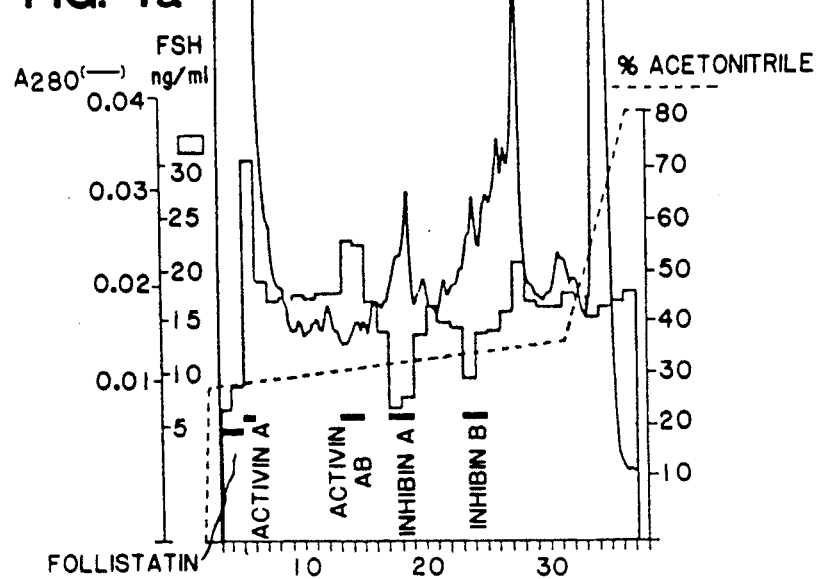
FIG. 1a shows RP-HPLC purification of the FSH release-inhibiting and FSH-releasing proteins recovered from gel filtration. The components of the active regions from the gel filtration, as determined by in vitro bioassay were pooled, lyophilized and, after dissolving in 0.2 N acetic acid, applied directly onto a Vydac $C_4$ column and eluted with the indicated gradient of acetonitrile in the TEAP buffer system at 3 ml/min. Two inhibin proteins, Inhibin A and B, follistatin and two activin proteins, indicated by the solid bars, were recovered.

Using a multi-step procedure, two peptides were isolated to substantial homogeneity from porcine follicular fluid (PFF). Each protein (Follistatin A and Follistatin B) is a monomer; they have molecular weights of about 35K and 32K. An amino acid analysis of the total protein has been performed for each, and the amino acid residue sequence of the amino-terminus of each chain has been determined by microsequencing and was found to be: Gly-Asn-Cys-Trp-Leu-Arg-Gln-Ala-Lys-Asn-Gly-Arg-Cys-Gln-Val-Leu. As a result of further work, it is believed that 35K Follistatin A has 315 amino acid residues and a free acid C-terminus. Follistatin B is believed to be a 288-residue free acid which is shortened at the C-terminus by 27 residues.

Each protein is acidic, having a pKa of about 5, and is generally soluble in aqueous media. Each is glycosylated to a limited extent, as determined by limited affinity to concanavalin A. Each protein exhibits inhibin activity in that it specifically inhibits basal secretion of FSH in a rat anterior pituitary monolayer culture system. Follistatin A exhibits a half-maximal inhibition of FSH release at a concentration of 2.5–6.0 ng/ml ($0.07$–$0.17 \times 10^{-9}$M). Follistatin B is statistically equipotent. Each protein is useful for regulating fertility of mammalian animals, particularly males.

In the purification procedure, porcine follistatin is isolated from crude extract material obtained from a porcine animal body, specifically porcine follicular fluid (PFF) although other appropriate bodily extracts might be used, by successive purification procedures that include heparin-Sepharose affinity chromatography, gel filtration and at least one and preferably several RP-HPLCs of different conditions of stationary phase and/or mobile phase. The same procedure is useful in obtaining a desired mammalian follistatin protein from a crude extract resulting from recombinant DNA processes.

In the preferred procedure by which porcine inhibin was first isolated to substantial purity, PFF was first purified by heparin-Sepharose affinity chromatography, next by gel filtration on Sephacryl S-200 gel and then with five successive RP-HPLCs using different mobile phase gradients and/or derivatized silica supports plus one step of ion exchange HPLC. Preferably stationary phases having relatively low hydrophobicity are used, with $C_3$–$C_8$ columns being preferred and $C_3$–$C_5$ and phenyl columns being particularly preferred. Solute specificity of the mobile phase is preferably adjusted by varying the concentration of an organic component, particularly acetonitrile. Although a single RP-HPLC fractionation significantly increases the purity relative to the gel-filtrated material, two or more, and preferably six, HPLC purifications are generally performed subsequent to successive treatment by heparin-Sepharose chromatography and gel filtration.

The starting material for the procedure was frozen PFF that was procured from J.R. Scientific, Woodland, CA. Approximately 18 liters of such frozen PFF were processed in 250 ml batches to isolate the follistatin. The first step of the purification was heparin-Sepharose affinity chromatography, in which the protein is adsorbed to the Sepharose-bound heparin moieties under application conditions, and the adsorbed follistatin material is recovered by 1M NaCl elution. This step greatly expedites the purification procedure for crude extracts because it allows a relatively large volume of a crude extract, such as PFF, to be processed fairly rapidly while recovering an amount of protein exhibiting total inhibin-like activity equal to at least 90% of that of the crude extract.

Throughout the purification procedure, the inhibin-like bioactivity was monitored by an in vitro bioassay using rat anterior pituitary monolayer culture, Vale, W. et al. *Endocrinology*, 91, 562–572 (1972). In brief, 21-day-old female rat anterior pituitaries are collected, enzymatically dispersed and plated in 10% fetal bovine serum in HDMEM (GIBCO Laboratories, Santa Clara, CA.) into 24-well tissue culture plates (Falcon Plastic, Oxnard, CA.) on day 1. On day 2, the medium is changed to 1% fetal bovine serum in HDMEM, and the sample is added. Incubation is continued for another 48 hours. The medium is then harvested, and the LH and FSH contents are determined by radio-immunoassay (RIA) using materials provided by The Pituitary Hormone Program of NIADDKD. In this assay, the follistatin and inhibin proteins inhibit the basal release of FSH only but not that of LH, as compared to control cells that receive the incubation medium only.

For the detection of such inhibin activity in the various column fractions, aliquots ranging from 0.01% to 0.1% by volume were removed, and after adding 100 $\mu$g human serum albumin in 100 $\mu$l water, the solvents were evaporated in a Speed-Vac concentrator (Savant, Hicksville, N.Y.). The residue was redissolved in 3 ml 1% fetal bovine serum in HDMEM, filtered through a Millex-GS 0.22 $\mu$m filter (Millipore Corp., Bedford, MA) and assayed in duplicate. To speed up the bioassays during the purification process, only basal inhibition of FSH secretion exerted by the follistatin and inhibin was determined and plotted in the region where such proteins were expected to migrate in the chromatograms.

To perform the heparin-Sepharose affinity chromatography, a 500 ml bottle of frozen PFF was defrosted, and the cell debris were spun down in a Beckman J2-21 centrifuge (Beckman Instruments, Inc., Palo Alto, CA.) using a JA-20 rotor at 10,000 rpm for 30 minutes. One half of the supernatant (250 ml) was diluted to 10 times its volume by the addition of 2,250 ml of 0.01 M Tris-HCl containing 0.1 M NaCl, pH 7, in a 4 liter Erlenmeyer flask and pumped simultaneously via eight silastic tubes (0.76mm ID) into eight heparin-Sepharose (Pharmacia Fine Chemicals, Piscataway, N. J.) columns (3.5×9 cm) by two Rabbit 4-channel peristaltic pumps (Rainin Instrument Co., Inc., Emeryville, CA.) at 40 ml/hr per column. After all the fluid had been pumped through the heparin-Sepharose, the eight columns were washed simultaneously with 3.5 liters of 0.01 M Tris-HCl, pH 7, containing 0.1 M NaCl in the same manner. The adsorbed proteins with inhibin activity were removed by washing the eight columns simultaneously with 1.3 liters of 0.01 M Tris-HCl containing 1 M NaCl, pH 7, as above, and the wash was collected into fractions of 16 ml. The inhibin activity was monitored by the in vitro bioassay described above. The columns were regenerated by further washing with 1.6 liters 2M NaCl in 0.01 M Tris-HCl, pH 7, and re-equilibrated with 3.5 liters 0.01 M Tris-HCl containing 0.1 M NaCl for purification of the remaining 250 ml of PFF.

Next, the material was fractionated by gel filtration to separate proteins generally according to their molecular weights. The fractions having such inhibin-like activity extracted by the eight heparin-Sepharose columns were pooled (400 ml) and dialyzed overnight to remove NaCl in a 28.6 mm cylinder diameter Spectrapor No. 3 membrane tubing with $M_r$ cutoff at 3,500 (Spectrum Medical Industries, Inc., Los Angeles, CA.) against 16 liters of 30% acetic acid. The retained fluid was centrifuged, as above, to remove a white precipitate, and the supernatant was divided into eight equal portions for applying to eight 5×100 cm Sephacryl S-200 superfine columns (Pharmacia Fine Chemicals, Piscataway, N. J.). Each column was eluted with 30% acetic acid at 20 ml for 22 min., and the column fractions were monitored by UV absorption at 280 nm and by bioassay.

The elution profile of the material purified in a Sephacryl S-200 column showed several elution zones exhibiting inhibin and FSH-releasing activity. These regions were selected for further purification by RP-HPLC and were accordingly pooled and lyophilized. The lyophilized material (40 mg) was dissolved in 40 ml 0.2N acetic acid and filtered through a Millex-HA 0.45 um filter (Millipore Corp., Bedford, MA.). The filtrate was applied directly onto a 1×25 cm Vydac 5-μm particle-size $C_4$ column (The Separation Group, Hesperia, CA.) and developed with a gradient of TEAP buffer. In the TEAP system, buffer A consists of 0.25 N. triethylammonium phosphate (TEAP), pH 3, and buffer B is 80% acetonitrile in buffer A. After all the filtrate had been loaded, the column was washed with the aqueous buffer A until the UV absorption reached baseline. The fractions exhibiting inhibin and FSH-releasing activity were separated in a Beckman 332 gradient liquid chromatography system (Beckman Instruments, Inc., Berkeley, CA.) equipped with a Spectroflow 757 UV detector (Kratos Analytical Instruments, Ramsey, N. J.), a Soltec 220 recorder (Soltec Corp., Sun Valley, CA.) and a Redirac 2112 fraction collector (LKB Instruments, Inc., Gathersburg, MD.). Three zones of substantial inhibin activity were detected with the earlier eluting zone being called follistatin and with the later eluting zones being inhibin A and inhibin B. Two zones of FSH-releasing factors were detected, which were later termed activin A and activin AB, a homodimer and a heterodimer, respectively. The follistatin zone eluted first, as shown in FIG. 1a, between the seventh and twelfth minutes of the gradient.

Figure 1B:
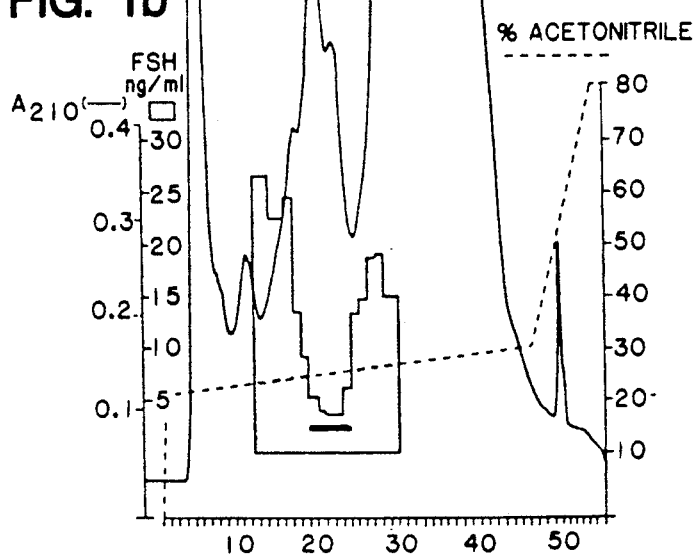
FIG. 1b shows the active fractions 3 and 4, designated by the solid bar labelled follistatin in FIG. 1a, which were pooled and, after being diluted to 3 times their original volume, applied directly onto a Vydac $C_4$ column and eluted with the indicated gradient of acetonitrile in trifluoroacetic acid (TFA) buffer system at 3 ml/min.
Figure 1C:
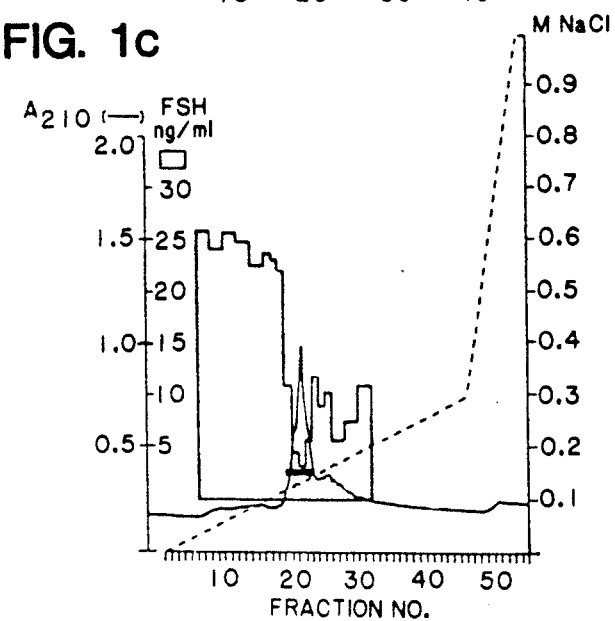
FIG. 1c shows the active material, denoted by the solid bar in FIG. 1b, which was pooled, and after removing the acetonitrile and adjusting to pH 6.5, applied to a Spherogel-TSK DEAE-5PW column and then eluted therefrom with the indicated gradient of sodium chloride in sodium phosphate buffer system at a rate of 1 ml/min.
Figure 2A:
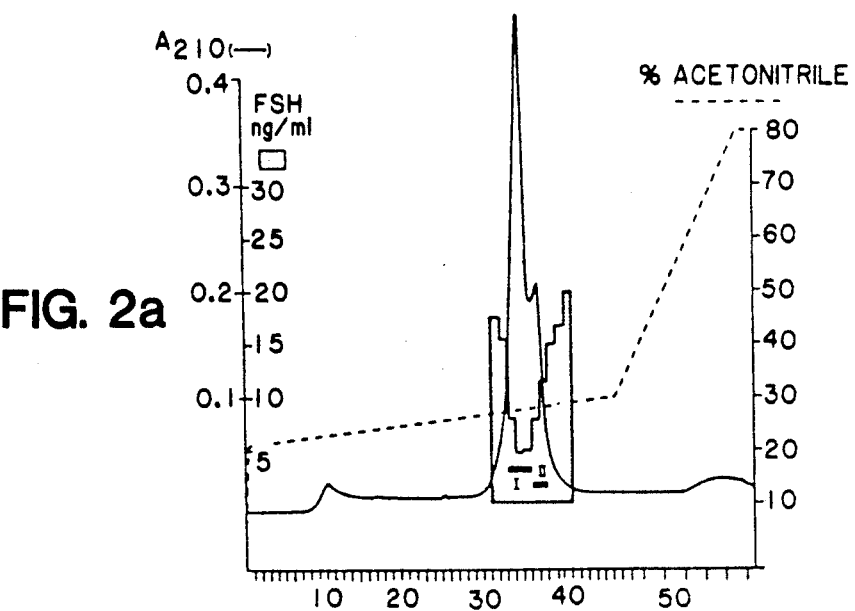
FIG. 2a shows the active material fractions from the column shown in FIG. 1c which were pooled and, after being diluted to 3 times their original volume, applied directly onto a Vydac $C_4$ column and eluted with the indicated gradient of acetonitrile in trifluoroacetic acid (TFA) buffer system at 1 ml/min.
Figure 2B:
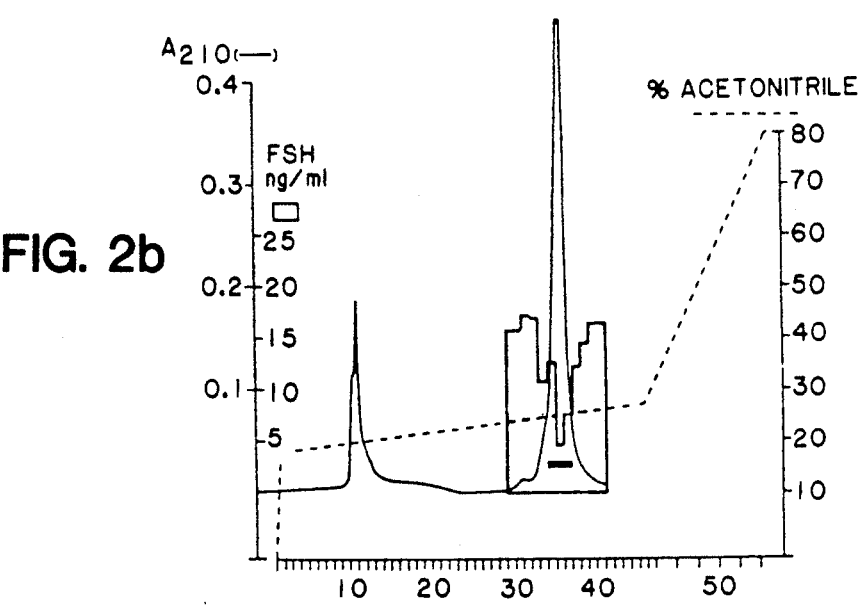
FIG. 2b shows the active material fractions from the column, denoted by the solid bar I in FIG. 2a, which were pooled, diluted to 3 times its original volume and likewise purified on a Vydac Phenyl column with the indicated gradient of acetonitrile in triethylammonium phosphate (TEAP) buffer system at 1 ml/min.
Figure 2C:
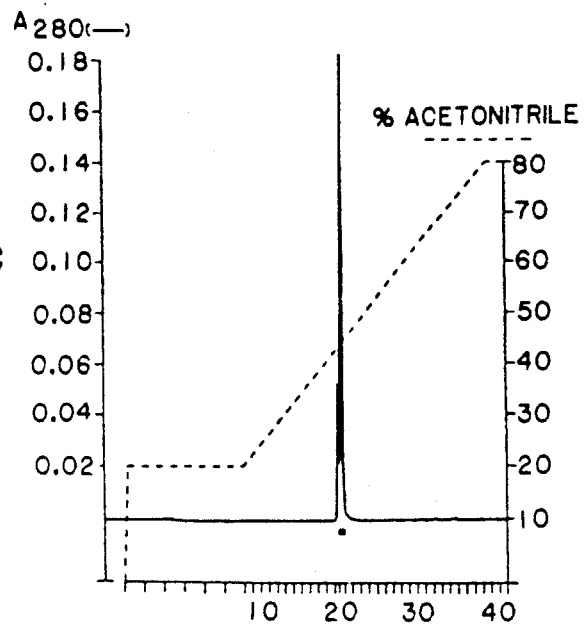
FIG. 2c shows the active material fractions from the column, represented by the solid bar in the chromatogram of FIG. 2b which were pooled and concentrated on an Aquapore RP-300 column with the indicated gradient of acetonitrile in the TFA buffer system at 0.5 ml/min.

Follistatin fractions from the column represented in FIG. 1a were pooled, mixed with an equal volume of 0.2N acetic acid and further purified by another RP-HPLC step which uses a 1×25 cm Vydac 5-μm-particle-size $C_4$ column and a trifluoroacetic acid (TFA) buffer system (FIG. 1b). In the TFA system, buffer A contains 1 ml trifluoroacetic acid in 999 ml water and buffer B is 1 ml trifluoroacetic acid in 199 ml water and 800 ml acetonitrile. The active material elutes from the column with a linear gradient of 21 to 30% acetonitrile in the TFA system in 90 min. at a flow rate of 3 ml/min. Fractions with FSH release-inhibiting activity (fractions 19-23) detected by the bioassay were pooled and, after removing the acetonitrile in a Speed-Vac concentrator (Savant, Hicksville, NY) and adjusting to pH 6.5 with 0.1 N ammonium hydroxide, were pumped directly onto a 7.5×75 mm Spherogel-TSK 10 μ DEAE-5PW column (Toyo Soda, Tokyo, Japan). After loading, the column was washed with buffer A until the UV absorption reached baseline. Buffer A was 0.1 M sodium hydrogen phosphate ($Na_2HPO_4$) pH 7.5. The follistatin activity was separated with a linear gradient of 0 to 0.3 M NaCl in Buffer A in 90 min at a flow of 1 ml/min as shown in FIG. 1c. The active material eluting in fractions 19 to 22 from the column was pooled and, after diluting to four times its original volume with 0.2 N acetic acid, further purified on a 1×25 cm Vydac 5 μ $C_4$ column and eluted with a linear gradient of 21 to 30% acetonitrile in the TFA solvent system in 90 min at a flow of 1 ml/min as shown in FIG. 2a. The active material eluting in fractions 33-35 (peak I) was pooled and diluted to twice its original volume and rechromatographed on a 10×250 mm Vydac 5 μ phenyl column with a linear gradient of 18 to 27% acetonitrile in the TEAP system in 90 min at a flow of 1 ml/min, as shown in FIG. 2b. Finally, the follistatin in fractions 34-36 was pooled and, after dilution with 0.2 N acetic acid, was concentrated by RP-HPLC using a 0.46×25 cm Aquapore RP-300 10 μm-particle-size column (Brownlee Labs., Santa Clara, CA.) using a linear gradient of 20 to 80% acetonitrile in the TFA buffer system as shown in FIG. 2c. Altogether, a total of approximately 400 μg of active material was isolated and purified from the 18 liters of PFF and termed Follistatin A.

Amino acid analyses of the substantially homogeneous Follistatin A was performed as described in Bohlen P., et al. *Anal. Biochem.* 126 144-152 (1982), and the results are shown in Table 1 below.

TABLE 1

AMINO ACID COMPOSITION OF PURIFIED FOLLISTATIN PROTEIN FROM PORCINE FOLLICULAR FLUID

| Amino Acid | Follistatin A* ($M_r$ 35,000) | Follistatin B* ($M_r$ 32,000) |
|---|---|---|
| Asx | 34.1 ± 0.2 | 28.4 ± 0.0 |
| Thr | 17.7 ± 0.3 | 15.9 ± 0.0 |
| Ser | 25.6 ± 0.2 | 22.2 ± 0.2 |
| Glx | 36.7 ± 0.1 | 31.1 ± 0.1 |
| Gly | 23.3 ± 0.2 | 24.5 ± 0.0 |
| Ala | 17.1 ± 0.2 | 15.6 ± 0.0 |
| Val | 15.5 ± 0.3 | 14.0 ± 0.0 |
| Met | 3.2 ± 0.1 | 3.4 ± 0.0 |
| Ile | 10.1 ± 0.1 | 7.5 ± 0.1 |
| Leu | 20.9 ± 0.2 | 19.1 ± 0.0 |
| Tyr | 9.5 ± 0.1 | 8.8 ± 0.1 |
| Phe | 5.0 ± 0.1 | 4.6 ± 0.0 |
| His | 2.2 ± 0.0 | 2.0 ± 0.0 |
| Trp | 5.8 ± 0.1 | 5.6 ± 0.1 |
| Lys | 26.2 ± 0.0 | 25.2 ± 0.1 |
| Arg | 12.7 ± 0.1 | 13.7 ± 0.1 |
| Cys** | 35.9 ± 0.2 | 33.5 ± 0.1 |
| Pro | 13.5 ± 0.3 | 13.0 ± 0.1 |

*Data corresponds to the mean ± SD of two analyses and normalized to a protein of 35,000 daltons for the $M_r$ 35,000 form of follistatin and a protein of 32,000 daltons for the $M_r$ 32,000 form.
**Cysteine was determined as cysteic acid after performic acid oxidation.

The Follistatin A from the final RP-HPLC purification was analyzed under reducing and non-reducing conditions in 1-mm-thick 10% acrylamide gel according to the method of Laemmli, U., *Nature* 227 1677-1685 (1970). The protein was revealed by silver staining reagent (BIO-RAD, Richmond CA.). The following molecular weight standards were used to calibrate the gel: bovine serum albumin ($M_r$=67,000), ovalbumin ($M_r$=43,000), alpha-chymotrypsinogen ($M_r$=25,700) and lysozyme ($M_r$=14,500). In non-reducing condition, 2 μg of Follistatin A in 20 μl water was incubated with 20 μl of buffer (0.152 M Tris-HCl, pH 6.8, containing 20% glycerol (V/V), 4% sodium dodecylsulfate and 0.04% bromphenol blue) for 1 hour at 37° C. prior to loading onto the gel. The electrophoresis was performed at a constant 200 volts for 6 hours at room temperature. In reducing condition, 2 μg of protein was incubated, first with 20 μl of 0.02 M dithiothreitol for 15 min at 37° C. and then 20 μl of the buffer was added, and the incubation continued for one more hour before the sample was applied to the gel. Electrophoresis was carried out as above, except that 0.005 M dithiothreitol was included in the electrophoretic buffer. On SDS-PAGE under non-reducing condition, Follistatin A showed a single band migrating at $M_r$ 35,000, and under reducing condition, it showed also a single band migrating at $M_r$ 42,000.

Using similar reversed-phase HPLC conditions, a $M_r$ 32,000 form, termed Follistatin B, was isolated from fractions 36–37 of FIG. 2a (peak II). Its amino acid composition is related to the $M_r$ 35,000 form (see Table 1), and upon reduction, this protein also migrated as a single band at $M_r$ 40,000.

NH2-terminal sequence analyses of the porcine Follistatins A and B (pFS-A and pFS-B), as described in Esch, F. *Anal. Biochem.* 136, 39–47, 1984, was carried out. Based upon the results from multiple sequencing analyses of both follistatins, the NH2-terminal residues of each are established as Gly-Asn-Cys-Trp-Leu-Arg-Gln-Ala-Lys-Asn- Gly-Arg-Cys-Gln-Val-Leu. The NH2-terminal residue sequence of Follistatin A continued with the residues Tyr-Lys-Thr-Glu-Leu-Ser-Lys-Glu.

Once a substantial portion of the sequence of follistatin is known, the mRNA encoding the protein can be isolated, and the cDNA can be synthesized by recombinant DNA techniques. Messenger RNA (mRNA) is obtained from ovarian tissues which produce follistatin, and then cDNA is synthesized from the mRNA by reverse transcription. The cDNA is inserted into a cloning vector which is used to transform a suitable host to create a cDNA library.

Based upon the known partial amino acid residue sequence, labelled oligonucleotides are synthesized for detecting corresponding cDNA. Because of the degeneracy of the genetic code, mixed hybridization probes are prepared and used as probes. The following two probes were used to select, from the library, cDNA clones that contain gene sequences encoding follistatin: 3'- ACC TGT CTC CTC CTA CAC TTA CTG TTG TGG GAC AAG TTC -5' and 3'-CTC GTC ATG GAC ACA CCG TTA CTA CCG CAC TGG ATG -5'. Thirteen clones hybridizing to both probes were identified and purified. cDNA libraries may also be screened by immunological expression assay with antibody raised against follistatin chains. Immunological expression assay may also be used to confirm screening with hybridization probes.

From 12 of the 13 selected clones, cDNA is excised with Eco RI and inserted into M13mp19 phage where they are subcloned for sequence analysis. As a result of the sequence analysis, it is deduced that there are two precursor proteins encoded, one of 344 amino acids and a C-terminally shortened version thereof of 317 amino acids. It is further concluded that these precursors result in the secretion of two mature FS proteins, one of which, Follistatin A, is a 315-residue monomer having the following sequence:

Gly-Asn-Cys-Trp-Leu-Arg-Gln-Ala-Lys-Asn-Gly-Arg-Cys-Gln- Val-Leu-Tyr-Lys-Thr-Glu-Leu-Ser-Lys-Glu-Glu-Cys-Cys-Ser- Thr-Gly-Arg-Leu-Ser-Thr-Ser-Trp-Thr-Glu-Glu-Asp-Val-Asn- Asp-Asn-Thr-Leu-Phe-Lys-Trp-Met-Ile-Phe-Asn-Gly-Gly-Ala- Pro-Asn-Cys-Ile-Pro-Cys-Lys-Glu-Thr-Cys-Glu-Asn-Val-Asp- Cys-Gly-Pro-Gly-Lys-Lys-Cys-Arg-Met-Asn-Lys-Lys-Asn-Lys- Pro-Arg-Cys-Val-Cys-Ala-Pro-Asp-Cys-Ser-Asn-Ile-Thr-Trp- Lys-Gly-Pro-Val-Cys-Gly-Leu-Asp-Gly-Lys-Thr-Tyr-Arg-Asn- Glu-Cys-Ala-Leu-Leu-Lys-Ala-Arg-Cys-Lys-Glu-Gln-Pro-Glu- Leu-Glu-Val-Gln-Tyr-Gln-Gly-Lys-Cys-Lys-Lys-Thr-Cys-Arg- Asp-Val-Phe-Cys-Pro-Gly-Ser-Ser-Thr-Cys-Val-Val-Asp-Gln- Thr-Asn-Asn-Ala-Tyr-Cys-Val-Thr-Cys-Asn-Arg-Ile-Cys-Pro- Glu-Pro-Thr-Ser-Ser-Glu-Gln-Tyr-Leu-Cys-Gly-Asn-Asp-Gly- Val-Thr-Tyr-Ser-Ser-Ala-Cys-His-Leu-Arg-Lys-Ala-Thr-Cys- Leu-Leu-Gly-Arg-Ser-Ile-Gly-Leu-Ala-Tyr-Glu-Gly-Lys-Cys- Ile-Lys-Ala-Lys-Ser-Cys-Glu-Asp-Ile-Gln-Cys- Thr-Gly-Gly- Lys-Lys-Cys-Leu-Trp-Asp-Phe-Lys-Val-Gly-Arg-Gly-Arg-Cys- Ser-Leu-Cys-Asp-Glu-Leu-Cys-Pro-Glu-Ser-Lys-Ser-Glu-Glu- Pro-Val-Cys-Ala-Ser-Asp-Asn-Ala-Thr-Tyr-Ala-Ser-Glu-Cys- Ala-Met-Lys-Glu-Ala-Ala-Cys-Ser-Ser-Gly-Val-Leu-Leu-Glu- Val-Lys-His-Ser-Gly-Ser-Cys-Asn-Ser-Ile-Ser-Glu-Asp-Thr- Glu-Glu-Glu-Glu-Glu-Asp-Glu-Asp-Gln-Asp-Tyr-Ser-Phe-Pro- Ile-Ser-Ser-Ile-Leu-Glu-Trp. This characterization is in agreement with the earlier analyses of the purified protein material obtained from PFF; the disparity between the number of residues and the measured value of 35K is accounted for by the presence of glycosylation. About 63% of the labelled Follistatin A was retained on the concanavalin A - Sepharose 4B affinity column which could be displaced with 0.2 M α-methyl-D- mannopyranoside, indicating that Follistatin A is glycosylated. It is believed that a carbohydrate moiety having a molecular weight of about 3000 daltons is attached likely to the side chain of an Asn residue, most likely either the residue in the 95-position or that in the 259-position. The other mature protein, Follistatin B, has the same sequence as Follistatin A but is shortened by 27 residues at its C-terminus. It may be nonglycosylated or may have a different glycosylation.

The purified proteins show half maximal inhibition of FSH release at concentrations of 2.5–6.0 ng/ml ($0.07$–$0.17 \times 10^{-9}$ M) which is about one-third of that of inhibin A. Both have no effect on the secretion of luteinizing hormone, growth hormone, prolactin, or thyroid stimulating hormone.

Because the inhibins from different species show great homologies, i.e., porcine, human, bovine, ovine and rat, it appeared certain that such homologous follistatins from other species could be deduced using the same probes as were employed in searching the porcine cDNA libraries. Alternatively, probes can be prepared using cDNA fragments of the gene sequence coding for porcine follistatin. Thus, the knowledge of the sequence of porcine follistatin allows the present-day molecular biologist to deduce the sequences of the follistatins of other species and to also prepare such hormones by the use of recombinant DNA technology.

A testicular λgtll cDNA library is screened with a cDNA probe encoding the first 317 amino acids of the porcine FS (pFS) precursor. Out of $8.1 \times 10^5$ phage plaques, 12 positive clones are obtained, and 8 are selected for sequencing by the dideoxy chain-termination method after subcloning into the M13mp19 vector. From the nucleotide sequences of the clones, it is determined that there is encoded an hFS precursor containing a 344 amino acid sequence which is highly homologous with the 344-residue pFS precursor, differing in only 6 residues. A similar, C-terminally-shortened precursor is also encoded by other clones.

To further delineate the origin of the two precursors, the hFS gene is cloned and sequenced from a human genomic library. Out of 1 million phage plaques, 3 positives are obtained by hybridization with the same porcine cDNA probe. Restriction mapping and nucleotide sequence analyses reveal that one clone, which is 19.1 kb in length, encodes nearly the whole human FS gene containing 5 exons. As depicted in FIG. 3, these 5 exons encode respectively the signal sequence and the first 4 domains of FS (I-IV). Another 15.0 kb clone contains only the last exon (V) encoding the last 27 C-terminal residues of the 344-residue precursor. The 5'-terminal sequence of the second clone could not be merged with the 3'-end of the longer clone to yield the complete gene sequence. Nevertheless, the overall genomic organization of human FS is postulated to be composed of a DNA sequence that is more than 5 kb in length with 6 exons interrupted by 5 introns at the locations indicated in FIG. 3. Aside from the first exon which encodes the signal sequence, the following 4 exons, encoding domains I to IV, are of approximately equal size. The first 29 amino acid residues of the precursor correspond to the putative signal sequence followed by 4 repeating domains specified by the 36 cysteines. The first 4 introns, where sequences have been determined completely, contain 2009, 430, 346, and 702 base pairs, respectively, all of which possess the consensus 5'-GT . . . AG-3' donor and acceptor splicing sites.

FIGS. 3 and 4 show the cloned cDNA sequences and the corresponding amino acid sequences of the 317 and 344 residue hFS precursors. The differences between pFS and hFS are shown in parentheses in FIG. 3 and in boxes in FIG. 4, with the corresponding residues in pFS shown just below the human residue in the particular location. The cDNA encoding preFS317 contains the stretch of nucleotides from 980 to 1243, whereas in the cDNA encoding preFS344 that stretch of nucleotides is spliced out. Two potential N-linked glycosylation sites in the precursor protein are marked by stars. Arrowheads indicate the positions where the five introns are inserted in the follistatin gene.

Comparison with the porcine structure shows that there are only 6 conservative amino acid substitutions between the two species with two of the substitutions occurring within the signal sequence. The precursor protein predicts two potential N-linked glycosylation sites at residues 95 and 259. In porcine FS, glycosylation at Asn(259) has been tentatively identified, whereas no carbohydrate chain was detected at Asn(95). Whether this mode of glycosylation will apply to human FS is not yet confirmed. Thus, the sequence of mature human follistatin protein has been deduced and is exactly the same as porcine for 311 of the 315 residues; the four differences between human and porcine follistatins are as follows: Arg instead of Lys in 134-position; Ala instead of Thr in the 171-position; Asp instead of Glu in the 247-position and in the 251-position. The sequence of mature rat FS has also been deduced. There are seven differences between rat FS and hFS for the 315 residue sequence, as follows: Lys instead of Arg in the 134-position; Ser instead of Ala in the 171-position; Ser instead of Tyr in the 176-position; Gly instead of Thr in the 222-position; Glu instead of Asp in the 293- and 300-positions; and Thr instead of Ile in the 312-position.

Substantially pure Follistatin A or B or the nontoxic salts thereof, combined with a pharmaceutically acceptable carrier to form a pharmaceutical composition, may be administered to mammals, including humans, either intravenously, subcutaneously, percutaneously, intramuscularly or orally for control of fertility. Administration of follistatin induces decreased fertility in female mammals and decreases spermatogenesis in male mammals. Administration of a sufficient amount of follistatin induces infertility in mammals and may also be useful for testing to diagnose infertility. It presently appears that FS is only expressed in gonadal tissue and the kidneys and may exhibit some additional biological activity associated with its expression in the kidneys.

Of the four domains of follistatin, three of them are homologous: the sequence between residues 66 through 135, the sequence between residues 139 through 210 and the sequence between residues 216 through 287. Peptide including the individual sequences of these domains are considered to have biological activity. Therefore, it is anticipated that the following peptides may desirably be individually prepared: porcine follistatin (66-135); porcine follistatin (139-210): porcine follistatin (216-287); human follistatin (66-135): and human follistatin (216-287).

Using conventional methods, such as those described in Cold Springs Harbor Laboratory Manual, T. Maniatis, et al. (1982), (hereinafter CSH), a synthetic hFS gene is constructed encoding the 315 residue, mature hFS. For example, oligonucleotides are synthesized on an applied B10 systems automatic synthesizer having overlapping complementary sequences. The overlapping oligonucleotides are fused to form a double-stranded DNA chain, gaps being filled in with DNA polymerase and with T4 ligase to produce nonchromasomal DNA encoding mammalian follistatin. Alternatively, the appropriate cDNA sequence from the clone, from which the hFS sequence was deduced, is treated with DNA polymerase to obtain the desired double-stranded DNA chain encoding the mature hFS protein.

Immediately 5' of the FS-encoding sequence in the sense strand is provided an ATG start signal, which results in an extraneous methionine being added to the N-terminus of the expressed polypeptide. Immediately 3' of the FS-encoding sequence is a stop signal. At the 5' end is an Eco RI overhang, and at the 3' end is a Sal I overhang, whereby the synthetic DNA strand is directly insertable in the Eco RI and Sal I site of the plasmid pUC8, described by Vieira et al. Gene 14, 259–268 (1982). The DNA strand is annealed into the pUC8 plasmid where it is under the control of the beta galactosidase promoter with the ATG start signal and the Shine Delgarno sequence retained in their natural orientation and association with the promoter.

The recombinant vector, designated hFS, is transformed into the DH-1 strain of E. Coli by the calcium chloride procedure, CSH, supra. The transformed E. Coli is cultured in L broth, and ampicillan-resistant strains are selected. Because the DNA chain is inserted into the plasmid in an orientation which is expected to lead to expression of protein product of the DNA chain, the ampicillin-resistant colonies are screened for reactivity with antiserum raised against hFS. These colonies are screened by the immunological method of Healfman et al., Proc. Natl. Acad. Sci. USA 80, 31–35 (1983), and colonies reacting positively with hFS antibody are further characterized. The cells are separated from their culture media and lysed to obtain their supernatent.

Supernatent from transformed cells is determined by RIA to be reactive with antibody raised against hFS.

100 ml. of cell supernatent is obtained, and hFS is purified therefrom using the method described hereinbefore. Approximately 0.01 mg. of hFS, purified to upwards of 98% by weight of total protein, is produced.

The biological activity of the synthetic hF, which contains the extraneous N-terminal methionine residue, is tested for biological activity by the ability of the synthetic hFS to exhibit inhibin activity by specifically inhibiting basal secretion of FSH in a rat anterior pituitary culture system, as described hereinbefore. The biological activity of synthetic hFS is substantially identical to natural, purified pFS.

The superfluous N-terminal residue is removable by partial chemical digestion with cyanogen bromide or phenyl isothiocyanate followed by treatment with a strong anhydrous acid, such as trifluoroacetic acid. However, this process attacks internal Met residues, and while providing some pFS having the natural protein structure, substantially reduces the total amount of biologically active protein. It is preferably removed enzymatically.

Furthermore, the plasmid hFS, amplified in one of the hFS-producing *E. Coli* clones, can be isolated and cleaved with *Eco* RI and *Sal* I. This digested plasmid is electrophoresed on an agarose gel allowing for the separation and recovery of the amplified hFS insert. The insert is then inserted into the plasmic pYEp, a shuttle vector which can be used to transform both *E. Coli* and *Saccharomyces cerevisiae* yeast. Insertion of the synthetic DNA chain at this point assures that the DNA sequence is under the control of a promoter, in proper reading frame from an ATG signal and properly spaced relative to a cap site. The shuttle vector is used to transform URA3, a strain of *S. cerevisiae* yeast from which the oratate monophosphate decarboxylase gene is deleted.

The transformed yeast is grown in medium to attain log growth. The yeast is separated from its culture medium, and cell lysates are prepared. Pooled cell lysates are determined by RIA to be reactive with antibody raised against hFS, demonstrating that a peptide containing hFS peptide segments is expressed within the yeast cells.

The invention provides certain polypeptides and makes them available for biological and therapeutic use. The production of hFS can be carried out in both prokaryotic and eukaryotic cell lines. While hFS synthesis can be demonstrated using either bacteria or yeast cell lines, the synthetic genes should be insertable for expression in cells of higher animals, such as mammalian tumor cells. Such mammalian cells may be grown, for example, as peritoneal tumors in host animals, and hFS harvested from the peritoneal fluid.

Although the above examples demonstrate that hFS can be synthesized through recombinant DNA techniques, they are not asserted to purport to maximize production. It is expected that subsequent selection of more efficient cloning vectors and host cell lines will increase the yield of hFS. Known gene amplification techniques of both eukaryotic and prokaryotic cells may be used to increase production.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

Follistatin should be administered under the guidance of a physician, and pharmaceutical compositions will usually contain an effective amount of the peptide in conjunction with a conventional, pharmaceutically-acceptable carrier. The dosage will vary depending upon the specific purpose for which the protein is being administered, and dosage levels in the range of about 0.1 to about 1 milligrams per Kg. of body weight may be used when the protein is administered on a regular basis as a male contraceptive.

Although the method of purification of follistatin has been described primarily in terms of isolation from PFF, follistatin can be similarly purified from other crude extracts. The term "crude extracts" as used herein refers to other mammalian body material in addition to follicular fluid, as well as to extracts from organisms including laboratory microorganisms, such as prokaryotes (e.g. *E. Coli*) and eukaryotes (e.g. *S. cerevisiae* yeast), which have been transformed by means of state of the art methodology to manufacture mammalian follistatin protein.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Particular features of the invention are emphasized in the claims which follow.

What is claimed is:

1. A substantially pure monomeric mammalian follistatin protein having a molecular weight of between about 35,000 or 32,000, having a pKa of about 5, and having an amino-terminal sequence beginning with H-Gly-Asn-Cys-Trp-Leu-Arg-Gln-Ala-Lys-Asn-Gly-Arg-Cys-Gln-Val-Leu, said protein specifically inhibiting basal secretion of follicle-stimulating hormone while not inhibiting basal secretion of luteinizing hormone.

2. A protein according to claim 1 which is porcine follistatin.

3. A protein according to claim 1 which is glycosylated.

4. A protein according to claim 1 wherein said amino terminal sequence begins H-Gly-Asn-Cys-Trp-Leu-Arg-Gln-Ala-Lys-Asn-Gly-Arg-Cys-Gln-Val-Leu-Tyr-Lys-Thr-Glu-Leu-Ser-Lys-Glu.

5. A protein according to claim 4, having an amino acid composition of about Asx 34.1, Thr 17.7. Ser 25.6, Glx 36.7, Gly 23.3, Ala 17.1, Val 15.5, Met 3.2, Ile 10.1, Leu 20.9, Tyr 9.5, Phe 5.0, His 2.2, Trp 5.8, Lys 26.2, Arg 12.7, Cys 35.9, and Pro 13.5.

6. A protein having the formula: H-Gly-Asn-Cys-Trp-Leu-Arg-Gln-Ala-Lys-Asn-Gly-Arg-Cys-Gln-Val-Leu-Tyr-Lys-Thr-Glu-Leu-Ser-Lys-Glu-Glu-Cys- Cys-Ser-Thr-Gly-Arg-Leu-Ser-Thr-Ser-Trp-Thr-Glu-Glu-Asp-Val-Asn-Asp-Asn-Thr-Leu-Phe-Lys-Trp-Met-Ile-Phe-Asn-Gly-Gly-Ala-Pro-Asn-Cys-Ile-Pro-Cys-L s-Glu-Thr-Cys-Glu-Asn-Val-A p-Cys-Gly-Pro-Gly-Lys-Lys-Cys-Arg-Met-Asn-Lys-Lys-Asn-Lys-Pro-Arg-Cys-Val-Cys-Ala-Pro-Asp-Cys-Ser-Asn-Ile-Thr-Trp-Lys-Gly-Pro-Val-Cys-Gly-Leu-Asp-Gly-Lys-Thr-Tyr-Arg-Asn-Glu-Cys-Ala-Leu-Leu-Lys-Ala-Arg-Cys-Lys-Glu-Gln-Pro-Glu-Leu-Glu-Val-Gln-Tyr-Gln-G y-Lys-Cys-Lys-Lys-Thr-Cys-Arg-Asp-Val-Phe-Cys-Pro-Gly-Ser-Ser-Thr-Cys-Val-Val-Asp-Gln-Thr-Asn-Asn-Ala-Tyr-Cys-Val-Thr-Cys-Asn-Arg-Ile-Cys-Pro-Glu-Pro-Thr-Ser-Ser-Glu-Gln-Tyr-Leu-Cys-Gly-Asn-Asp-Gly-Val-Thr-Tyr-Ser-Ser-Ala-Cys-His-Leu-Arg-Lys-Ala-Thr- ys-Leu-Leu-Gly-Arg-Ser-Ile-Gly-Leu-Ala-Tyr-Glu-Gly-Lys-Cys-Ile-Lys-Ala-Lys-Ser-Cys-Glu-Asp-Ile-Gln-Cys- Thr-Gly-Gly-Lys-Lys-Cys-Leu-Trp-Asp-Phe-Lys-Val-Gly-Arg-Gly-Arg-Cys-Ser-Leu-Cys-Asp-Glu-Leu-Cys-Pro-Glu-Ser-Lys-Ser-Glu-Glu-Pro-Val-Cys-Ala-Ser-Asp-Asn-Ala-Thr-Tyr-Ala-Ser-Glu-Cys-Ala-Met-Lys-Glu-Ala-Ala-Cys-Ser-Ser-Gly-Val-Leu-Leu-Glu-Val-Lys-His-Se -Gly-Ser-Cys-Asn-Ser-Ile-Ser-Glu-Asp-Thr-Glu-Glu-Glu-Glu-Glu-Asp-Glu-Asp-Gln-Asp-Tyr-Ser-Phe-Pro-Ile-Ser-Ser-Ile-Leu-Glu-Trp-OH or a shortened fragment thereof which is biologically active to inhibit basal secretion of FSH, said fragment being shortened by elimination of a sequence of residues beginning at the C-terminus or beginning at the N-terminus or both.

7. A protein according to claim 6 which is shortened by a sequence of about 27 residues beginning at the C-terminus.

8. A protein according to claim 1 having an amino acid composition of about Asx 28.4, Thr 15.9. Ser 22.2, Glx 31.1, Gly 24.5, Ala 15.6, Val 14.0, Met 3.4, Ile 7.5, Leu 19.1, Tyr 8.8, Phe 4.6, His 2.0, Trp 5.6, Lys 25.2, Arg 13.7, Cys 33.5, and Pro 13.0.

9. A protein according to claim 8 wherein said protein has an N-terminal sequence beginning H-Gly-Asn-Cys-Trp-Leu-Arg-Gln-Ala-Lys-Asn-Gly-Arg-Cys-Gln-Val-Leu.

10. A protein according to claim 1 which is human fillistatin.

11. A protein according to claim 10 which is glycosylated.

12. A protein having the formula: H-Gly-Asn-Cys-Trp-Leu-Arg-Gln-Ala-Lys-Asn-Gly-Arg-Cys-Gln-Val-Leu-Tyr-Lys-Thr-Glu-Leu-Ser-Lys-Glu-Glu-Cys-Cys-Ser-Thr-Gly-Arg-Leu-Ser-Thr-Ser-Trp-Thr-Glu-Glu-Asp-Val-Asn-Asp-Asn-Thr-Leu-Phe-Lys-Trp-Met-Ile-Phe-Asn-Gly-Gly-Ala-Pro-Asn-Cys-Ile-Pro-Cys-L s-Glu-Thr-Cys-Glu-Asn-Val-Asp-Cys-Gly-Pro-Gly-Lys-Lys-Cys-Arg-Met-Asn-Lys-Lys-Asn-Lys-Pro-Arg-Cys-Val-Cys-Ala-Pro-Asp-Cys-Ser-Asn-Ile-Thr-Trp-Lys-Gly-Pro-Val-Cys-Gly-Leu-Asp-Gly-Lys-Thr-Tyr-Arg-Asn-Glu-Cys-Ala-Leu-Leu-Lys-Ala-Arg-Cys-Lys-Glu-Gln-Pro- lu-Leu-Glu-Val-Gln-Tyr-Gln-Gly-Lys-Cys-Lys-Lys-Thr-Cys-Arg-Asp-Val-Phe-Cys-Pro-Gly-Ser-Ser-Thr-Cys-Val-Val-Asp- ln-Thr-Asn-Asn-Ala-Tyr-Cys-Val-Thr-Cys-Asn-Arg- Ile-Cys-Pro-Glu-Pro-Thr-Ser-Ser-Glu-Gln-Tyr-Leu-Cys-Gly-Asn-Asp-Gly-Val-Thr-Tyr-Ser-Ser-Ala-Cys-His-Leu-Arg-Lys-Ala-Thr-Cys-Leu-Leu-Gly-Arg-Ser-Ile-Gly-Leu-Ala-Tyr-Glu-Gly-Lys-Cys-Ile-Lys-Ala-Lys-Ser-Cys-Glu-Asp-Ile-Gln-Cys-Thr-Gly-Gly-Lys-Lys-Cys-Le -Trp-Asp-Phe-Lys-Val-Gly-Arg-Gly-Arg-Cys-Ser-Leu-Cys-Asp-Glu-Leu-Cys-Pro-Glu-Ser-Lys-Ser-Asp-Glu-Pro-Val-Cys-Ala-Ser-Asp-Asn-Ala-Thr-Tyr-Ala-Ser-Glu-Cys-Ala-Met-Lys-Glu-Ala-Ala-Cys-Ser-Ser-Gly-Val-Leu-Leu-Glu-Val-Lys-His-Ser-Gly-Ser-Cys-Asn-Ser-Ile-Se -Glu-Asp-Thr-Glu-Glu-Glu-Glu-Glu-Asp-Glu-Asp-Gln-Asp-Tyr-Ser-Phe-Pro-Ile-Ser-Ser-Ile-Leu-Glu-Trp-OH or a shortened fragment thereof which is biologically active to inhibit basal secretion of FSH, said fragment being shortened by elimination of a sequence of residues beginning at the C-terminus or beginning at the N-terminus or both.

13. A protein according to claim 12 which is shortened by a sequence of about 27 residues beginning at the C-terminus.

14. A protein produced by recombinant DNA techniques comprising a mammalian follistatin beginning with the N-terminal sequence: H-gly-Asn-Cys-Trp-Leu-Arg-Gln-Ala-Lys-Asn-Gly-Arg-Cys-Gln-Val-Leu and having a molecular weight about 32,000 Daltons or about 35,000 Daltons and a pKa of about 5, which follistatin molecule specifically inhibits basal secretion of follicle-stimulating hormone while not inhibiting basal secretion of leutinizing hormone.

15. A protein according to claim 14 wherein said amino terminal sequence begins H-Gly-Asn-Cys-Trp-Leu-Arg-Gln-Ala-Lys-Asn-Gly-Arg-Cys-Gln-Val-Leu-Tyr-Lys-Thr-Glu-Leu-Ser-Lys-Glu-Glu-Cys-Cys-Ser-Thr-Gly-Arg-Leu-Ser-Thr.

16. A protein according to claim 14 having the approximate amino acid composition: Asx 34.1, Thr 17.7, Ser 25.6, Glx 36.7, Gly 23.3, Ala 17.1, Val 15.5, Met 3.2, Ile 10.1, Leu 20.9, Tyr 9.5, Phe 5.0, His 2.2, Trp 5.8, Lys 26.2, Arg 12.7, Cys 35.9, and Pro 13.5.

* * * * *

UNITED STATES PATENT AND TRADEMARK OFFICE
CERTIFICATE OF CORRECTION

PATENT NO.   : 5,041,538

DATED        : August 20, 1991

INVENTOR(S)  : Ling, et al.

It is certified that error appears in the above-identified patent and that said Letters Patent is hereby corrected as shown below:

Column 1, as an initial paragraph, please insert:   --This invention was made with Government support under Grant Nos. HD-09690 and DK-18811, and Contract No. N01-HD-6-2944 awarded by the National Institutes of Health. The Government has certain rights in this invention.--  Column 11, line 7, change "hF" to --hFS--. IN THE CLAIMS: Column 13, line 4, change "L s" to --Lys--; line 4, change "A p" to --Asp--; line 10, change "G y" to --Gly--; line 15, change "ys" to --Cys--; line 22, change "Se" to --Ser--; line 43, correct the spelling of "follistatin". Column 14, line 2, change "L s" to --Lys--; line 7, change "lu" to --Glu--; line 8, change "Lys", first occurrence, to --Arg--; line 9, change "ln" to --Gln--; line 11, change "Thr" to --Ala--; line 16, change "Le" to --Leu--; line 17, change "Glu", second occurrence, to --Asp--; line 21, change "Se" to --Ser--; line 33, change "gly" to --Gly--.

Signed and Sealed this

Twenty-third Day of February, 1993

Attest:

STEPHEN G. KUNIN

*Attesting Officer*     *Acting Commissioner of Patents and Trademarks*